(12) United States Patent
Hu et al.

(10) Patent No.: US 8,076,638 B2
(45) Date of Patent: Dec. 13, 2011

(54) DRIFT TUBE STRUCTURE FOR ION MOBILITY SPECTROMETER

(75) Inventors: Haifeng Hu, Beijing (CN); Yuanjing Li, Beijing (CN); Qingjun Zhang, Beijing (CN); Zhiqiang Chen, Beijing (CN)

(73) Assignee: Nuctech Company Limited, Beijing (CN)

( * ) Notice: Subject to any disclaimer, the term of this patent is extended or adjusted under 35 U.S.C. 154(b) by 181 days.

(21) Appl. No.: 12/343,194

(22) Filed: Dec. 23, 2008

(65) Prior Publication Data

US 2009/0166532 A1 Jul. 2, 2009

(30) Foreign Application Priority Data

Dec. 29, 2007 (CN) .......................... 2007 1 0308546

(51) Int. Cl.
*H01J 49/00* (2006.01)
(52) U.S. Cl. .................. 250/288; 250/286; 250/287
(58) Field of Classification Search .............. 250/288
See application file for complete search history.

(56) References Cited

U.S. PATENT DOCUMENTS

| | | | |
|---|---|---|---|
| 4,855,595 A | 8/1989 | Blanchard | |
| 5,189,301 A | 2/1993 | Thekkadath | |
| 5,200,614 A | 4/1993 | Jenkins | |
| 6,051,832 A * | 4/2000 | Bradshaw | 250/286 |
| 6,509,562 B1 * | 1/2003 | Yang et al. | 250/287 |
| 6,727,495 B2 | 4/2004 | Li | |
| 6,897,437 B2 * | 5/2005 | Fuhrer et al. | 250/287 |
| 7,081,621 B1 * | 7/2006 | Willoughby et al. | 250/288 |
| 7,223,969 B2 | 5/2007 | Schultz et al. | |

OTHER PUBLICATIONS

Office Action issued in the corresponding Chinese application No. 200710308546.3 with summary of the Chinese Office Action in English, Oct. 30, 2009.
Office Action issued in the corresponding German application No. 102008064130.8 with English translation of the German Office Action, Jan. 19, 2011.

* cited by examiner

*Primary Examiner* — Phillip A Johnston
(74) *Attorney, Agent, or Firm* — Knobbe, Martens, Olson and Bear LLP

(57) ABSTRACT

A drift tube structure for ion mobility spectrometer is disclosed comprising electrode sheets and insulation parts arranged in alternation, with each electrode sheet being a mesh metal sheet having a radian or taper portion which is convexly curved toward an ion input. Further, the radian or taper portion of the electrode sheet has meshes of higher transparency. With the above structure of the present invention, an electric field having a periphery of uniform focusing center can be formed in the migration zone. The circular ring configuration of the electric field periphery can shield the migration electric field from any influence of external electric fields. The electrodes are each meshlike and have a circular hole at the center, thus they can focus and collect as many as possible ions that do not move along the central axis, and those ions moving along the central axis can pass through the electrodes transparently.

5 Claims, 3 Drawing Sheets

US 8,076,638 B2

DRIFT TUBE STRUCTURE FOR ION MOBILITY SPECTROMETER

CROSS REFERENCE TO RELATED APPLICATIONS

This application claims priority under 35 U.S.C. Section 119 to Chinese application 200710308546.3, filed on Dec. 29, 2007. This application is hereby incorporated by reference in its entirety.

BACKGROUND OF THE INVENTION

1. Field of Invention

The present invention relates to the field of safety inspection technology, in particular to a drift tube structure used in inspection equipment for inspecting drugs and explosives by means of ion mobility technique.

2. Description of Prior Art

Ion mobility spectrometer discriminates different ions according to a fact that different ions have different drift velocities in a uniform weak electric field. The ion mobility spectrometer is usually formed of a sample input section, an ionization section, an ion gate or an ion storage section, a migration zone, a collection zone, a sensing circuit, a data acquisition and processing and control section, etc.

In the existing techniques, to achieve a higher ion transmittance, attention has been paid to ion focusing technology. A time-variable electric field is used in focusing in U.S. Pat. No. 4,855,595. Cup-shaped electrodes are used in focusing to increase ion transmittance in U.S. Pat. No. 5,189,301. Unfortunately, a considerable quantity of ions may be scattered to the electrodes and disappear. In U.S. Pat. No. 6,727,495, a time-variable electric field, for which electrode sheets are divided in even number with a phase difference of 90 degrees between adjacent electric fields of divided sheets, is coupled with a linear electric field to focus the ions and thus increase ion transmittance. This technique has the disadvantage of complex structure and control. In U.S. Pat. No. 7,223,969, a method of alternating between strong and weak static electric fields is adopted in ion focusing to increase ion transmittance. Again, this method results in complex structure.

FIG. 1 shows a drift tube structure in the prior art. It comprises a sample input unit 1, a semi-permeable film, an ionization source 2, an ion gate 3, a drift tube 4, a Faraday tray 5 and a front circuitry 5, etc., arranged in this order. The internal electric field of the drift tube is susceptible to interference, and the peripheral ions are often scattered and disappear due to the electric field having a non-uniform edge.

SUMMARY OF THE INVENTION

An object of the present invention is to provide a drift tube structure which can improve ion transmittance for the drift tube in a simple and efficient way.

In one aspect of the present invention, a drift tube structure for ion mobility spectrometer is provided comprising electrode sheets and insulation parts arranged in alternation, with each electrode sheet being a mesh metal sheet having a radian or taper portion which is convexly curved, preferably toward an ion input.

Preferably, the radian or taper portion of the electrode sheet has meshes of higher transparency.

Preferably, the center of the electrode sheet is a hole having a diameter in the order of millimeter.

Preferably, the center of the electrode sheet is a circular hole.

Preferably, the periphery of the electrode sheet is a metal configuration having metal rings on one or both sides.

Preferably, the electrode sheet close to Faraday plate has a smaller center hole than the electrode sheet far away from the Faraday plate.

Preferably, the insulation part is formed in a ring shape.

Preferably, the electrode sheets are arranged coaxially at equal or unequal interval and applied with increment or decrement voltages.

With the above structure of the present invention, an electric field having a periphery of uniform focusing center can be formed in the migration zone. The circular ring configuration of the electric field periphery can shield the migration electric field from any influence of external electric fields. The electrodes are each mesh-like and have a circular hole at the center, thus they can focus and collect as many as possible ions that do not move along the central axis, and those ions moving along the central axis can pass through the electrodes transparently. The electrodes close to the Faraday plate have smaller center holes. This configuration allows the pass-through of focused ion beams on one hand, and, on the other hand, can shield the Faraday plate from any influence of previous ion movement at these electrodes, thereby dramatically increasing ion transmittance. Since the ion beam is very thin, the Faraday plate can be made very small. This leads to reduced input capacitance of the front circuitry and less circuit noise.

BRIEF DESCRIPTION OF THE DRAWINGS

The above advantages and features of the present invention will be apparent from the following detailed description taken conjunction with the drawings in which.

DETAILED DESCRIPTION OF PREFERRED EMBODIMENTS

Now, preferred embodiments of the present invention will be described with reference to the figures, in which the same reference symbol, though shown in different figures, denotes the same or like component. For the purpose of clarity and simplicity, detailed description of known functions and structures incorporated here will be omitted, otherwise it may obscure the subject matter of the present invention.

Figure 1:
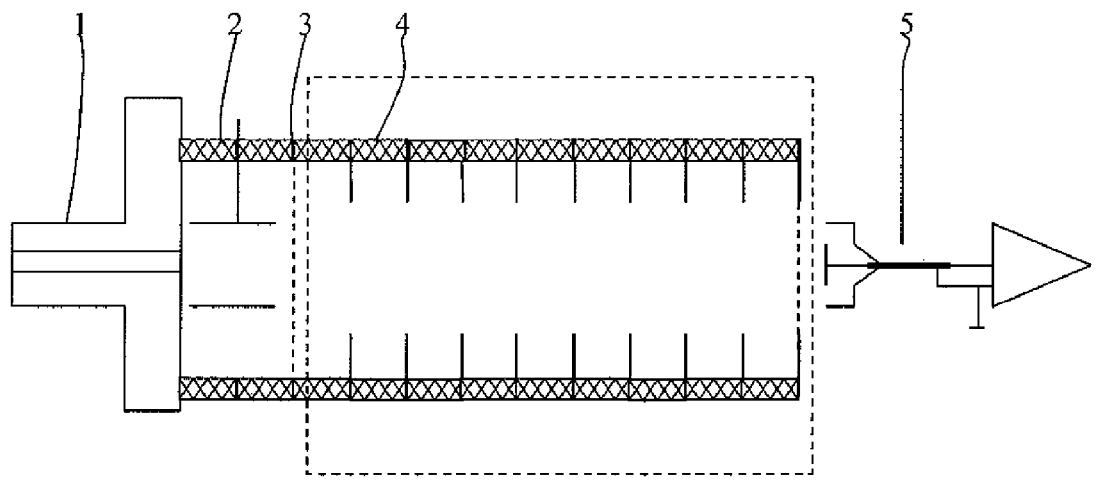
FIG. 1 is a schematic sectional diagram of a drift tube structure in the prior art.
Figures 2A, 2B, 2C, 2D, 2E, 2F, 2G:
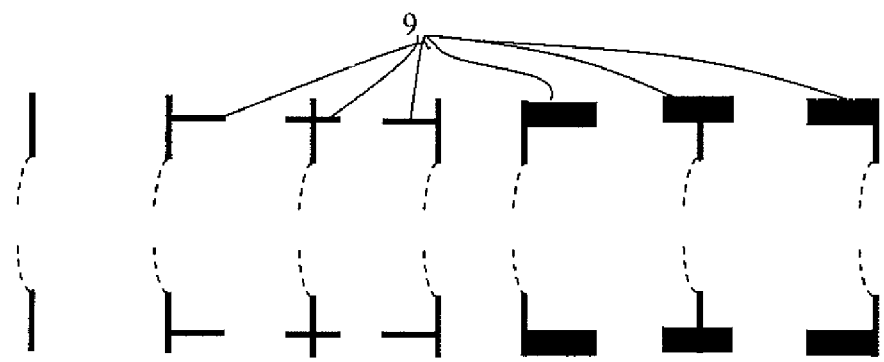
FIG. 2 and FIGS. 2A to 2G are schematic diagrams of a mesh electrode configuration used in a drift tube according to an embodiment of the present invention.
Figure 2:
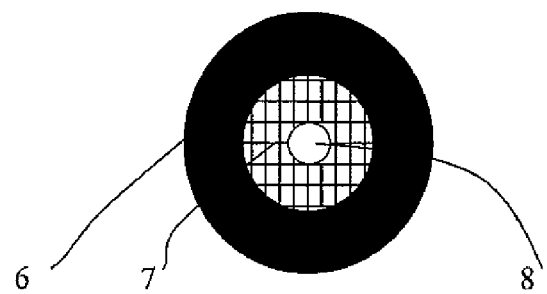

Referring to FIG. 2, the electrodes used in the drift tube of the present embodiment are each a mesh metal sheet having a radian or taper portion including the mesh radian or taper portion 7 of the electrode sheet, for example. The portion 7 is convexly curved toward an ion input. The death zone has very thin metal threads. The center 8 of the electrode sheet is a circular hole or a hole of any other shape. The periphery 6 of the electrode sheet is a metal configuration 9 having metal circular rings or rings of any other shape, such as square can, on one or both sides. The electrode close to the Faraday plate will generally have a smaller center hole 8 than the electrode far away from the Faraday plate.

FIG. 2A shows a schematic sectional view of the electrode whose periphery portion does not have any metal circular ring. FIGS. 2B, 2C and 2D each show a schematic sectional view of the electrode whose periphery portion has metal circular rings. Such electrode is suitable for a larger insulator. FIGS. 2E, 2F and 2G each show a schematic sectional view of the electrode whose periphery portion has metal circular rings of great thickness. Such electrode is suitable for a smaller insulator.

Figures 3A, 3B, 3C, 3D, 3E, 3F, 3G:
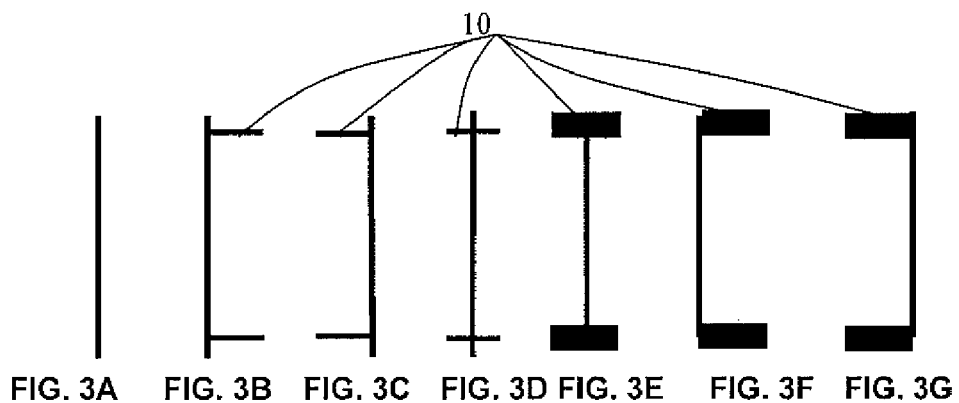
FIG. 3 and FIGS. 3A to 3G are schematic diagrams of an electrode configuration that can be used together with the mesh electrode according to an embodiment of the present invention.
Figure 3:
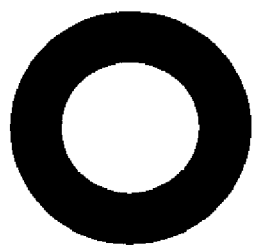

FIG. 3 shows a ring electrode that can be used together with the mesh electrode in the drift tube according to the embodiment of the present invention. The ring electrode can have a periphery with or without shield mechanism 10. The ring electrode can be used with the mesh electrode in an alternating manner to optimize performance and cost.

Figure 4:
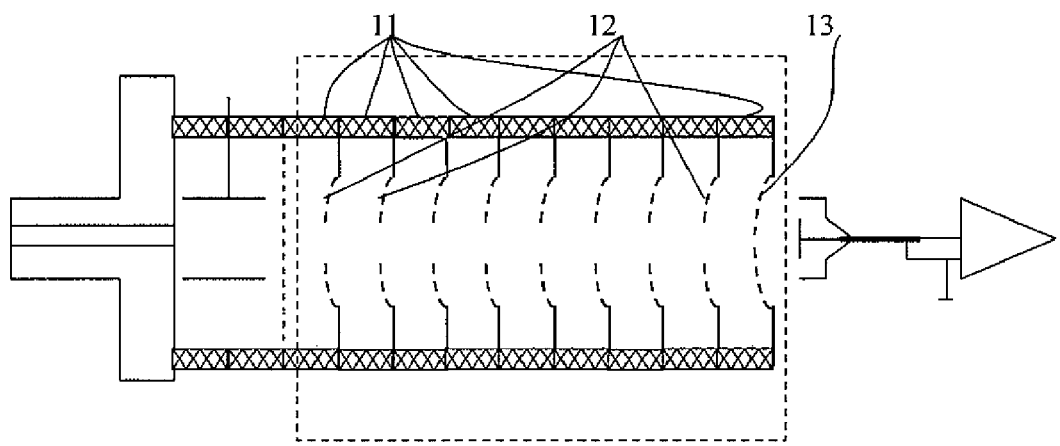
FIG. 4 is a schematic diagram of the configuration of a drift tube according to an embodiment of the present invention.
Figure 5:
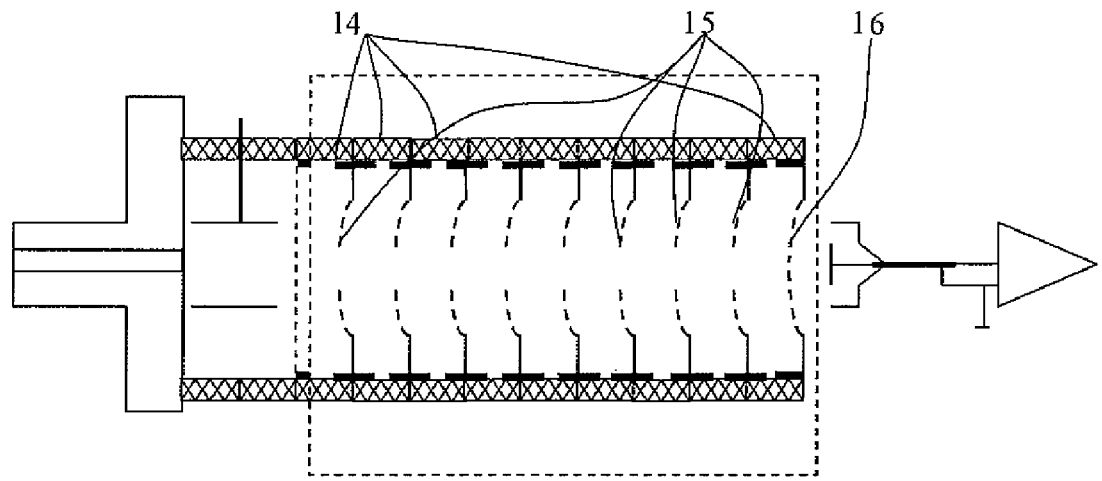
FIG. 5 is a schematic diagram of the configuration of a drift tube according to an embodiment of the present invention.
Figure 6:
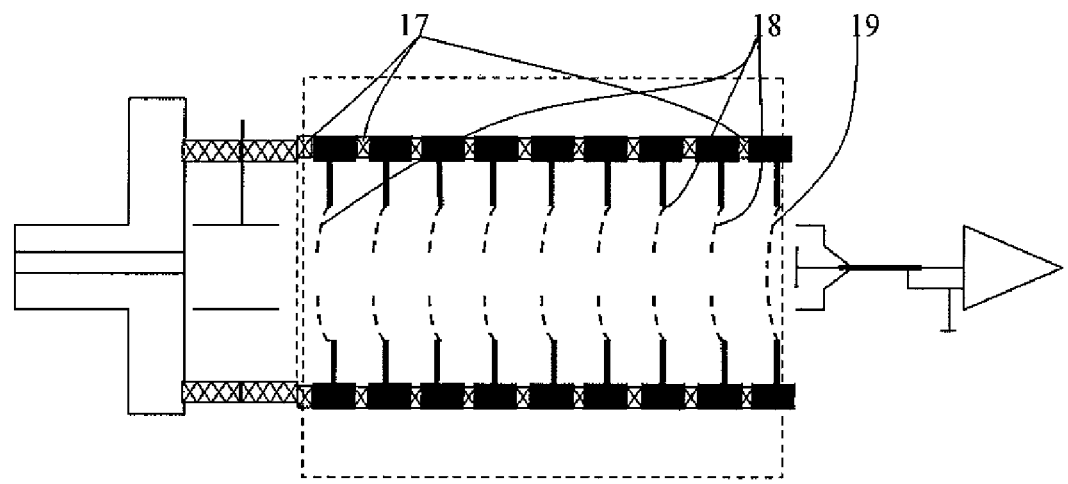
FIG. 6 is a schematic diagram of the configuration of a drift tube according to an embodiment of the present invention.

Now turning to FIGS. 4, 5 and 6, the electrodes 12, 15, 18 are formed by the electrodes of the shapes shown in FIGS. 2A, 2C, 2F, respectively. The electrodes 13, 16, 19 closer to the Faraday plate are also formed by the electrodes of the shapes shown in FIGS. 2A, 2C, 2F, respectively, and each of them has a smaller center hole 8. Among these electrodes, the insulators 11, 14, 17 are disposed between two adjacent electrodes.

The foregoing description is only the preferred embodiments of the present invention and not intended to limit the present invention. Those ordinarily skilled in the art will appreciate that any modification or substitution in the principle of the present invention shall fall into the scope of the present invention defined by the appended claims.

What is claimed is:

1. A drift tube structure for ion mobility spectrometer, comprising electrode sheets and insulation parts arranged in alternation, with each electrode sheet being a mesh metal sheet having a radial or taper portion which is convexly curved toward an ion input, wherein the radial or taper portion of the electrode sheet has meshes of higher transparency and the center of the electrode sheet is a circular hole such that ions moving along a central axis of the drift tube can pass through the electrode sheets transparently.

2. The drift tube structure of claim 1, wherein the periphery of the electrode sheet is a metal configuration having metal rings on one or both sides.

3. The drift tube structure of claim 1, wherein the electrode sheet close to Faraday plate has a smaller center held hole than the electrode sheet far away from the Faraday plate.

4. The drift tube structure of claim 1, wherein the insulation part is formed in a ring shape.

5. The drift tube structure of claim 1, wherein the electrode sheets are arranged coaxially and applied with incremental or decremental voltages.

* * * * *